United States Patent

Ulick

Patent Number: 4,603,128
Date of Patent: Jul. 29, 1986

[54] MINERALOCORTICOID HORMONE ANTAGONISTS

[76] Inventor: Stanley Ulick, 38 Crane Rd., Scarsdale, N.Y. 10583

[21] Appl. No.: 636,404

[22] Filed: Jul. 31, 1984

[51] Int. Cl.⁴ ............................................. A01N 45/00
[52] U.S. Cl. ................................ 514/169; 260/397.3; 260/397.4; 260/397.47
[58] Field of Search .................... 514/169; 260/397.3, 260/397.4, 397.47

[56] References Cited

U.S. PATENT DOCUMENTS 2,904,560  9/1959  Dodson et al. ................. 260/397.47

OTHER PUBLICATIONS

Schaub et al., "Journal of Organic Chemistry (1961) pp. 3915–3925.

Primary Examiner—Elbert L. Roberts

Attorney, Agent, or Firm—Stiefel, Gross, Kurland & Pavane

[57] ABSTRACT

7α-acylthio-4-pregnene-3,20-diones, active as mineralocorticoid hormone antagonists, of the formula:

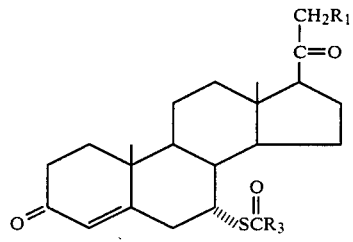

in which $R_1$ is hydrogen, hydroxyl or acyloxy —$OR_2$, $R_2$ is an acyl group derived from a straight or branched-chain alkyl, alkenyl, alkynyl, cycloalkyl, cycloalkenyl, aryl or heterocyclic carboxylic acid having up to 12 carbon atoms.

11 Claims, No Drawings

MINERALOCORTICOID HORMONE ANTAGONISTS

TECHNICAL FIELD

This invention relates to a new class of mineralocorticoid antagonists and their use for the treatment of clinical disorders associated with inappropriate or excessive secretion of mineralocorticoid hormones. These disorders include sodium-retaining edema states, hypertension, hypokalemia and adrenal tumors.

BACKGROUND ART

The therapeutic use of an agent to block inappropriate or excessive secretion of endogenous adrenocortical sodium-retaining, potassium-excreting (mineralocorticoid) hormones in various disorders in man is well established. One such mineralocorticoid antagonist and potassium-sparing diuretic, spironolactone U.S.P., has been in clinical use for more than 25 years. Despite its efficacy, the administration of spironolactone leads to the undesirable side effects of gynecomastia and impotence in men and menstrual irregularities in women. In addition, its tumorogenicity in long-term studies in rodents has led the Food and Drug Administration (F.D.A. Drug Bulletin, p. 33, August–October 1976) to recommend restriction of the use of spironolactone to patients in whom other therapy is inadequate. Such side effects are considered to be the result of interaction of the drug with gonadal steroid hormone biosynthetic and target cell receptor systems (the occurrence of such side effects can be predicted by measuring their cross-reactivity toward mammalian androgen target cell receptors).

Dodson and Tweit, in U.S. Pat. No. 2,904,560, described a group of 7α-acylthio-4-pregnene-3,20-diones which were said to possess both hormonal and anti-hormonal activities consisting of cortisone-like (anti-inflammatory) and progestational hormonal activity, and inhibition of the sodium-retaining effects of desoxycorticosterone. The patent does not disclose which acylthio derivatives are glucocorticoid or progestational hormones and which are mineralocorticoid anti-hormones (it is recognized that all of these activities are unlikely to reside in a single compound).

Two 7α-acetylthio-4-pregnenediones found useful in the practice of the present invention, namely 7α-acetylthio-4-pregnene-3,20-dione and 7α-acetylthio-21-acetoxy-4-pregnene-3,20-dione, have previously been described by R. E. Schaub and M. J. Weiss, J. Org. Chem. 26:3915, 1961, but without any disclosure of possible therapeutic applications.

DISCLOSURE OF THE INVENTION

It has been found that certain 7α-acetylthio-4-pregnene-3,20-diones are more active mineralocorticoid antagonists and less active androgen antagonists than spironolactone. These 7α-acetylthio pregnenediones are more effective in blocking the action of aldosterone but less prone to cause antiandrogenic side effects. The discovery of this class of mineralocorticoid antagonists rest on the observation that certain substitutions in ring B of the steroid ring system lead to reversal of biological activity and the transformation of a hormone into an antihormone. Substitution by a 7α-acylthio group and, in particular, 7α-acetylthiolation converts the potent naturally-occurring minearalocorticoid agonist 11-deoxycorticosterone and certain of its derivatives, into potent mineralocorticoid antagonists capable of blocking the effect of excessive or inappropriate mineralocorticoid secretion in mammals.

The compounds within the scope of this invention are represented by Formula I:

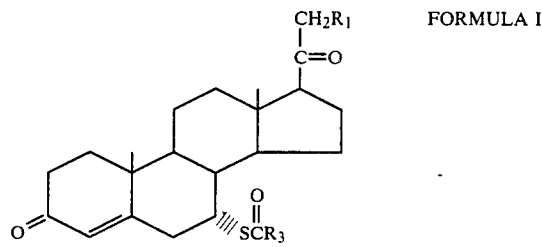

FORMULA I in which $R_1$ is hydrogen, hydroxyl, a mineral acid ester such as a sulfate, phosphate or nitrate group, or acyloxy —$OR_2$, the acyl group $R_2$ being derived from a carboxylic acid of the formula $R_4COOH$ which may have up to 12 carbon atoms, and in which $R_4$ may be substituted or unsubstituted, saturated or unsaturated, straight chain or branched alicyclic, aryl, heterocyclic or mixed, and $R_3$ is methyl.

The compounds within the scope of the above formula which are novel per se are those where $R_1$ is hydroxyl or $OR_2$ where $R_2$ is derived from a carboxylic acid of the above type, but having one or from 3 to 12 carbon atoms. In other words, with the exception of $R_1=H$ and $R_1=$acetoxy, the compounds found useful as mineralocorticoid hormone antagonists in this invention are themselves novel.

7α-acetytlthio substitution accomplishes two important objectives. In the 21-hydroxy and 21-acyloxy-4-pregnene-3,20-dione series it transforms mineralocorticoid agonists into antagonists while retaining very high mineralocorticoid receptor affinity-several times greater than that of spironolactone.

A second advantage of the substitution is enhancement of bioavailability by inhibiting the $\Delta^4$-3-keto reductases of liver and kidney which normally convert biologically active steroid hormones to inactive tetrahydro metabolites. The enhanced bioavailability imparted by the 7α-acetylthio substituent leads to high activity by the parenteral route of administration in keeping with the in vitro activity, and in addition, provides efficacy by the oral route, a property of the ring B-substituted 11-deoxycorticosterones which the parent hormone itself does not possess. A further advantage of the corticosteroid derived mineralocorticoid antagonists of this invention is their negligible cross-reactivity toward the androgen receptor. Thus, they are not expected to show the anti-androgen side effects of the androgen-derived spirolactones in general and of spironolactone in particular.

It has, however, been found that substantial mineralocorticoid activity is not a general property of 7α-acylthio-4-pregnene-3,20-diones, but is rather quite narrowly limited to a specific subclass lacking oxygenated substitutents at the 11, 14, 15 or 17 positions of the steroid ring system. Such class of active materials excludes the several materials exemplified in the Dodson and Tweit patent referred to above.

BEST MODE FOR CARRYING OUT THE INVENTION

The 7α-acetylthio derivatives employed in the practice of the present invention include the otherwise unsubstituted 7α-acylthio-4-pregnene-3,20-dione (wherein $R_1$ in the above formula is hydrogen), the 21-hydroxy derivative thereof (wherein $R_1$ is hydroxyl), and the ester derivatives wherein $R_1$ is acyloxy —$OR_2$, and $R_2$ is an acyl group derived form a carboxylic acid of the formula $R_4COOH$ containing up to 12 carbon atoms, in which $R_4$ may be saturated or unsaturated, straight or branched chain, alicyclic, aryl, heterocyclic or mixed.

The unsubstituted 7α-acetylthio- and the 21-acetoxy-7-acetylthio-pregnenediones can be prepared as described by Schaub and Weiss. The C-21 hydroxy derivative can be prepared by hydrolysis of the 21-acetoxy compound by conventional techniques, e.g., with alcoholic alkali. The further C-21 acyloxy derivatives can also be prepared by conditions known in the art, for example, by reacting the alcohol with an acid or an acid halide in the presence of an esterification catalyst such as p-toluene sulfonic acid, p-toluene sulfonyl chloride, trifluoroacetic acid, or anhydrous sulfuric acid or, preferably, with the corresponding acid anhydride in the presence of pyridine or an amine. Acids which may be thus reacted include alkanoic acids, e.g., acetic, propionic, butyric, valeric, hexanoic, lauric, trimethylacetic, isobutyric, isovaleric or tertiary butylacetic acid; cycloaliphatic acids, e.g., β-bicyclopentylpropionic, cyclohexanecarboxylic or cyclohexylacetic acid; alkaryl acids, e.g., benzoic, phenylacetic, β-phenylpropionic or o-, m- or p-toluic acid; saturated dibasic acids (which can be converted to sodium or other water soluble salts), e.g., succinic or adipic acids; monobasic unsaturated acids, e.g., acrylic, crotonic, undecylenic, propionic, 2-butynoic, undecenoic or cinnamic acids; dibasic unsaturated acids (which can be converted to sodium or other water soluble salts) e.g., maleic or citraconic acids; or other organic substituted acids, e.g., lactic, mandelic, salicyclic, trifluoroacetic, chloroacetic, α- or β-bromopropionic, iodobenzoic, thioglycolic, α-aminopropionic, benzenesulfonic, toluenesulfonic, 2-furoic or like acids.

The C-21 esters may also be prepared by converting the C-21 alcohols to the corresponding carbonate esters by reaction with an alkyl chloroformate in the presence of pyridine. The ester moiety may also be formed by reaction with an appropriate mineral acid such as phosphoric acid, nitric acid, sulfuric acid, sulfonic acid or sulfinic acid.

Preferred among the aldosterone antagonists of the invention are the 21-lower alkanoyloxy esters of the 7α-acetylthio-4-pregnene-3,20 diones of the above formula, where $R_1$=$OR_2$ and $R_2$ is acyl, especially acetyl, propionyl, n-butyryl, n-valeryl, pivalyl and n-heptanoyl. These compounds have been found to exhibit particularly high levels of aldosterone antagonist activity.

The aldosterone antagonists of this invention may be utilized in dosages substantially lower than (e.g., one-half or less) that required for aldosterone antagonists of the spirolactone type (see for example under Aldactone, Physicians Desk Reference p. 1838, 1984). They may be administered in any suitable dosage form, e.g., formulated with any known organic or inorganic pharmaceutical carrier. Carriers so utilized should be inert relative to the steroid. The aldosterone antagonists are preferably orally administered, for example, in tablets, capsules or the like. If desired, the preparations may be sterilized for parenteral use or may additionally contain known auxiliary substances, such as preserving, stabilizing, wetting or emulsifying agents, salts for regulating osmotic pressure, buffers, extenders and/or other conventional carriers or the like. The active ingredient in these preparations, such as an ampoule or a tablet, may be incorporated within the range of from about 5 to 50 milligrams.

The following examples illustrate the preparation of preferred mineralocorticoid hormone antagonists of the invention, and describe the in vitro and in vivo pharmacological testing thereof. In the examples all parts and percentages are given by weight, and all temperatures are specified in degrees Celsius, unless otherwise indicated.

PREPARATIONS

General

Thioacylation of 3-keto-4, 6-pregnadienes took place almost quantitatively when the steroids were dissolved in excess thioalkanoic acid and maintained at room temperature for 18 hours. Reaction mixtures were routinely worked up by removal of excess reagent under vacuum and recrystallization of the product from either methanol, acetone or ethyl acetate. The products of smaller scale reactions were purified by preparative scale reversed phase high performance liquid chromatography. Appropriate ultraviolet absorption maxima were observed at 238–240 nm for 3-keto-4-pregnenes and at 282–284 nm for 3-keto-4,6-pregnadienes. The structures of all synthesized compounds were confirmed by the observation of a molecular ion using either electron impact, chemical ionization or secondary ion mass spectrometry. In addition all bioassayed compounds were homogeneous by high performance chromatography.

4-6-Pregnadiene-2,20-diones

The 6-dehydro derivatives were prepared from progesterone, 11-deoxycorticosterone acetate and cortisol acetate using chloranil in t-butanol-acetic acid under reflux, as described by E. T. Agnello and G. D. Laubach (J. Amer. Chem. Soc. 82:4293 1960). Physical constants of the purified products, 4,6-pregnadiene-3,20-dione, 21-acetoxy-4,6-pregnadiene-3,20-dione, and 11β,17α-dihydroxy 21-acetoxy-4,6-pregnadiene-3,20-dione agreed with the literature.

EXAMPLE 1

7α-Acetylthio-4-pregnene-3,20-dione

The reaction of 50 mg 4,6-pregnadiene-3,20-dione with 0.3 ml ethanethiolic acid carried out and worked up as described above afforded the 7α-acetylthio derivative crystallized from acetone, m.p. 184°–185° in agreement with the literature (R. E. Schaub and J. Weiss, J. Org, Chem. 26:3915, 1961). A chromatographically homogeneous sample isolated by preparative high performance liquid chromatography gave $M^+ = 388$ daltons.

EXAMPLE 2

7α-Acetylthio-21-hydroxy-4-pregnene-3,20-dione

The product of Example 3 was hydrolyzed by treating 0.5 g of the 21-acetoxy derivative in 8 ml methylene chloride with 10 ml methanol and 4 ml 0.2M aqueous potassium carbonate at room temperature under nitrogen for 30 minutes. The hydrolyzed product was extracted with methylene chloride, washed with water, dried and evaporated. A sample obtained by preparative high performance liquid chromatography showed $M^+ = 404$ daltons. An identical product was obtained by a different synthetic route involving alkaline hydrolysis of 21-acetoxy-4,6-pregnadiene-3,20-dione to the C-21-alcohol, followed by reaction with ethanethiolic acid.

EXAMPLE 3

7α-Acetylthio-21-acetoxy-4-pregnene-3,20-dione

The reaction of 1 gram 21 acetoxy-4,6-pregnadiene-3,20-dione and 2.0 ml ethanethiolic acid gave the 7α-acetylthio derivative with a m.p. 104°–106° when crystallized from acetone, in agreement with Schaub and Weiss, and a higher melting form, m.p. 160°–161° when recrystallized from methanol. Preparative high performance liquid chromatography separated the major product (the 7α-acetylthio isomer) from a trace isomeric component (the 7β-acetylthio form). A chromatographically homogeneous sample of 7α-acetylthio-21-acetoxy-4-pregnene-3,20-dione showed $M^{30} = 446$ daltons.

EXAMPLES 4–8

Higher C-21 esters of 7α-acetylthio-21-hydroxy-4-pregnene-3,20-dione

The product of Example 2 was reacted in 100 mg portions with 0.25 ml of a series of anhydrides in 0.5 ml dry pyridine at room temperatures for 18 hours; completion of esterification was determined by chromatography. Excess reagents were removed under vacuum and the C-21-ester products isolated by preparative liquid chromatography. Identification and properties of the C-21 esters are summarized in Table 1:

TABLE 1

Preparation of C-21 esters of 7α-acetylthio-21-hydroxy-4-pregnene-3,20-dione

| Example | Acid Anhydride | C-21 ester product | max ethanol nm | $M^+$ Daltons |
|---|---|---|---|---|
| 4 | n-propionic | n-propionate | 240 | 460 |
| 5 | n-butyric | n-butyrate | 238 | 474 |
| 6 | n-valeric | n-valerate | 240 | 488 |
| 7 | trimethyl acetic | trimethyl-acetate | 238 | 488 |
| 8 | n-heptanoic | n-heptanoate | 238 | 516 |

CONTROLS A and B

7α-Propionylthio-4-pregnene-3,20-dione
7α-Propionylthio-21-acetoxy-4-pregnene-3,20-dione Propionylthio derivatives were prepared by the reaction of propanethiolic acid with the respective 6-dehydro derivatives in a manner analogous to that described in Example 1 respecting the reaction with ethanethiolic acid. 7α-propionylthio-4-preg nene-3,20-dione (Control A) and 7α-propionylthio-21-acet oxy-4-pregnene-3,20-dione (Control B) obtained in this manner showed physical constants in agreement with those reported by Dodson and Tweit (J. Amer. Chem. Soc. 81:1227, 1959 and U.S. Pat. No. 2,904,560).

CONTROLS C and D

7α-Propionylthio-21-butyroxy-4-pregnene-3,20-dione
7α-Propionylthio-21-heptanoyloxy-4-pregnene-3,20-dione
7α-Propionylthio-21-hydroxyl-4-pregnene-3,20-dione The 21-acetoxy derivative (Control B) was treated with potassium carbonate in the manner described in Example 3 and the hydrolyzed product, the C-21-alcohol, was isolated in pure form by preparative high performance liquid chromatography and its structure compared by mass spectrometry, $M^+ = 418$ daltons. An identical product was obtained by the reaction of 21-hydroxy-4,6-preg nadiene-3,20-dione with propanethiolic acid.

Control C

Esterification of 25 mg of the above alcohol with 0.1 ml n-butyric anhydride and 0.2 ml dry pyridine at room temperature for 18 hours followed by the usual work-up and isolation of the product by high performance liquid chromatography gave the C-21 n-butyrate ester, confirmed by mass spectrometry showing $M^+ = 488$ daltons.

Control D

The procedure of Control C was applied using n-heptanoic anhydride instead of n-butyric anhydride; the ester product was isolated in the same way and was confirmed to be the C-21-heptanoate ($M^+ = 530$ daltons).

CONTROL E

7α-Acetylthio-21-acetoxy-11β-dihydroxy-4-pregnene-3,20-dione

Included among the group of compounds described by Dodson and Tweit (U.S. Pat. No. 2,904,560) as inhibiting the sodium-retaining effect of 11-deoxycorticosterone were 7-acetylthio derivatives of glucocorticoid steroids. To determine whether 7-thioacylation could transform potent glucocorticoid agonists into mineralocorticoid antagonists, the 7α-acetylthio derivative of cortisol acetate (Example 6 of the patent) was prepared and tested for mineralocorticoid antagonism. The 6-dehydro derivative of cortisol acetate, obtained as described above, was reacted with ethanethiolic acid under the same conditions used in Examples 1–3 above. Following the usual work-up, the product was isolated by preparative high performance liquid chromatography, and crystallized from acetone; the product gave physical constants in agreement with the literature.

BIOLOGICAL TESTING

Mineralocorticoid receptor affinity

The several test and control compounds were tested for their affinity for the mineralocorticoid receptor of mammalian kidney using the procedure of Grekin and Sider (J. Steroid Biochem. 13:835, 1980) as modified by Ulick, Land and Chu (Endocrinology 113:2320, 1983), to determine the ability of the various compounds to compete with aldosterone. Each assay tube contained 250 μl cytosol solution and 1,2-$^3$H-aldosterone at a final steroid concentration of $1.3 \times 10^{-9}$M. Standard curves were prepared in the range of 0.1 to 100 ng aldosterone and non-specific binding of $10^{-5}$M aldosterone was subtracted. The amount of steroid ligand required to effect 50% reduction in the binding of labeled aldosterone compared to the amount of aldosterone to effect the same reduction was expressed as a percentage.

Androgen receptor affinity

The relative affinity of test substances for the androgen receptor was taken as a measure of androgen antagonist activity and of the potential for anti-androgen side effects. A standard preparation of the cytosolic androgen receptor from female mouse kidney was used in an assay as described by Wright, Chan and Bardon (Endocrinology 108:2210, 1981) using 200 mg tissue per ml of molybdate-containing tris buffer (pH 7.4) medium. For the androgen receptor assay, each tube contained 200 μl cytosol and 5 nM $^3$H-17α-methyltrienolone as the androgen binding ligand, and the test steroids in the range of 0.05 to 500 ng in 200 ul buffer. In addition, each assay tube also contained 250 ng dexamethasone to saturate glucocorticoid receptor sites. The amount of test steroid required to achieve a 50% reduction in androgen receptor binding compared to the amount of 17α-methyltrienolone to achieve the same effect was expressed as a percentage.

Mineralocorticoid antagonism in vivo

The bioassay for anti-mineralocorticoid activity was carried out as described for the assay of mineralocorticoid agonist activity by Ulick, Land and Chu, (Endocrinology 99:619, 1976), except that the control group received 1 μg of aldosterone per 100 g body weight and the experimental group received the test substance in addition. All results were expressed as ratio of control urinary Na/K to treatment urinary Na/K. The minimum effective dose of antagonist was defined as that amount of test substance required to block one-half of the effect of 1 μg. aldosterone/100 g body weight as measured by the ratio of control: treatment urinary Na/K.

Table 2 summarizes mineralocorticoid and androgen receptor affinities individually and their ratios as a measure of the therapeutic index of mineralocorticoid antagonist potency in relation to the potential for anti-androgen mediated side effects. All eight acetylthio pregnenediones tested exhibited greater mineralocorticoid receptor affinity and less androgen receptor affinity than spironolactone. This affinity ratio index was almost 40 times greater for Example 3 as compared with spironolactone.

TABLE 2

Comparison of mineralocorticoid and androgen receptor affinities of spirono-lactone and substances of Examples, 1–8

| Substance | Formula I substituent | | | Corticosteroid Receptor % | | Affinity Mineralo-corticoid: Androgen Ratio |
| --- | --- | --- | --- | --- | --- | --- |
| | $R_1$ | $R_2$ | $R_3$ | Mineralo-corticoid | Androgen | |
| Spironolactone | | | | 18 | 2.0 | 9.0 |
| 1 | H | | $CH_3$ | 43 | 0.25 | 172 |
| 2 | OH | | $CH_3$ | 35 | 0.2 | 175 |
| 3 | $OR_2$ | Acetyl | $CH_3$ | 65 | 0.2 | 325 |
| 4 | $OR_2$ | Propionyl | $CH_3$ | 38 | 0.2 | 190 |
| 5 | $OR_2$ | n-Butyryl | $CH_3$ | 60 | 0.2 | 300 |
| 6 | $OR_2$ | n-Valeryl | $CH_3$ | 68 | 0.2 | 340 |
| 7 | $OR_2$ | n-Heptanoyl | $CH_3$ | 27 | 0.15 | 180 |
| 8 | $OR_2$ | Pivalyl | $CH_3$ | 45 | 0.15 | 300 |
| Testosterone | | | | | 51 | |
| Aldosterone | | | | 100 | 0.1 | |

Mineralocorticoid antagonism

The relative effects of 7α-acylthio and C-21 ester substitution on mineralocorticoid antagonist activity relative to spironolactone are shown in Table 3. The 7α-acetylthio derivatives of Examples 1–8 were all more active than spironolactone in the in vivo assay. In addition, when corresponding 7α-acetylthio and 7α-propionylthio derivatives with the same substituents at C-21 were compared (compare the effects of the compounds of Examples 1,3,5 and 7 with those of Controls A, B, C and D, respectively), the 7α-acetylthio derivatives were always more active. Two of the Control test substances of Table 3, the 7α-thiopropionyl-4-pregnene-3,20-dione-21-heptanoate (Control D) and the 7α-acetylthio derivative of cortisol acetate (Control E) were inactive as antagonists at the highest does tested (250 μg/100 g):

TABLE 3

Comparison of in vivo mineralocorticoid antagonist activities in adrenalectomized rat assay

| Substance | Formula I substituent | | | Mineralocorticoid antagonism Minimum effective dose μg/100 g* |
| --- | --- | --- | --- | --- |
| | $R_1$ | $R_2$ | $R_3$ | |
| Spironolactone | | | | 250 |
| EXAMPLE | | | | |
| 1 | H | | $CH_3$ | 100 |
| 2 | OH | | $CH_3$ | 75 |
| 3 | $OR_2$ | Acetyl | $CH_3$ | 25 |
| 4 | $OR_2$ | Propionyl | $CH_3$ | 100 |
| 5 | $OR_2$ | n-Butyryl | $CH_3$ | 50 |
| 6 | $OR_2$ | n-Valeryl | $CH_3$ | 150 |
| 7 | $OR_2$ | n-Heptanoyl | $CH_3$ | 75 |
| 8 | $OR_2$ | Pivalyl | $CH_3$ | 75 |
| CONTROL | | | | |
| A | H | | $CH_2CH_3$ | 200 |
| B | $OR_2$ | Acetyl | $CH_2CH_3$ | 100 |
| C | $OR_2$ | n-Butyryl | $CH_2CH_3$ | 150 |
| D | $OR_2$ | n-Heptanoyl | $CH_2CH_3$ | inactive |
| E | 7α-Acetylthiocortisol acetate | | | inactive |

*Results are expressed as minimum dose required to reduce urinary Na/K of rats receiving 1 μg aldosterone alone to one half. Units are μg antagonist administered subcutaneouly along with 1 μg aldosterone expressed per 100 g. body weight. Inactive compounds showed no antagonist activity at a dose of 250 μg/100 g.

Oral efficacy

As shown in Table 4 below, the 7α-acetylthio-21-acetoxy pregnenedione mineralocorticoid antagonist (Example 3) was 10 times more effective than spironolactone by the subcutaneous route of administration. The bioavailability conferred by ring B substitution was apparent from the oral route of administration as well; as shown in Table 4, a four-fold greater dose of spironolactone than the 7α-acetylthiopregnenedione was required for an equivalent mineralocorticoid antagonist effect:

TABLE 4

Effect of route of administration on the in vivo mineralocorticoid antagonist activity of spironolactone and the compound of Example 3

| Substance | Mineralocorticoid antagonism Minimum effective dose | |
|---|---|---|
| | subcutaneous | oral |
| | μg/100 g | |
| Spironolactone | 250 | 1000 |
| Example 3: 21-acetoxy-7α-acetylthio-4-pregnene-3,20-dione | 25 | 250 |

It will be understood that various changes may be made in the embodiments described herein without departing from the scope of the present invention. Thus, any prohormone structure differing from the compounds described above but capable of transformation by body processes from or to such compounds is within the scope of the invention. Accordingly, the foregoing description of the preparation and use of preferred forms of the process and the compositions of the present invention should be construed as illustrative only, it being intended that the invention be limited only in accordance with the claims appended hereto.

What is claimed is:

1. A process for blocking the effect of mineralocorticoids on a mammal, which comprises administering an effective amount of a mineralocorticoid hormone antagonist selected from the group consisting of 7α-acetylthio-4-pregnene-3,20-diones of the formula:

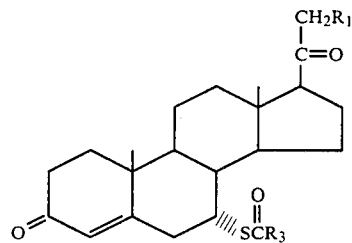

in which $R_1$ is hydrogen, hydroxyl, a mineral acid ester, or acyloxy —$OR_2$;

$R_2$ is an acyl group from a carboxylic acid of the formula $R_4COOH$ having up to 12 carbon atoms and in which $R_4$ is straight or branched-chain alkyl, alkenyl, alkynyl, cycloalkyl, cycloalkenyl, aryl or heterocyclic; and $R_3$ is methyl.

2. The process of claim 1, wherein the mineralocorticoid hormone antagonist is a compound wherein $R_1$ is hydrogen, hydroxy or a monocarboxylic, straight or branched-chain alkanoyloxy group having up to 12 carbon atoms.

3. The process of claim 1, wherein the mineralocorticoid hormone antagonist is a compound wherein $R_1$ is hydrogen, hydroxy, acetoxy, propionyloxy, n-butyryloxy, trimethylacetoxy, n-valeroyloxy or n-heptanoyloxy.

4. The process of claim 1, wherein the mineralocorticoid hormone antagonist is 7α-acetylthio-4-pregnene-3,20 dione.

5. The process of claim 1, wherein the mineralocorticoid hormone antagonist is 7α-acetylthio-21-hydroxy-4-pregnene-3,20-dione.

6. The process of claim 1, wherein the mineralocorticoid hormone antagonist is 7α-acetylthio-21-acetoxy-4-pregnene-3,20-dione.

7. The process of claim 1, wherein the mineralocorticoid hormone antagonist is 7α-acetylthio-21-propionyloxy-4-pregnene-3,20-dione.

8. The process of claim 1, wherein the mineralocorticoid hormone antagonist is 7α-acetylthio-21-n-butyryloxy-4-pregnene-3,20dione.

9. the process of claim 1, wherein the mineralocorticoid hormone antagonist is 7α-acetylthio-21-trimethylacetoxy-4-pregnene-3,20dione.

10. The process of claim 1, wherein the mineralocorticoid hormone antagonist is 7α-acetylthio-21-n-valeroyloxy-4pregnene-3,20-dione.

11. The process of claim 1, wherein the mineralocorticoid hormone antagonist is 7α-acetylthio-21-heptanoyloxy-4-pregnene-3,20-dione.

* * * * *